United States Patent
Smith et al.

(10) Patent No.: US 11,364,384 B2
(45) Date of Patent: Jun. 21, 2022

(54) COCHLEAR IMPLANTS HAVING IMPACT RESISTANT MRI-COMPATIBLE MAGNET APPARATUS

(71) Applicant: ADVANCED BIONICS AG, Staefa (CH)

(72) Inventors: James George Elcoate Smith, Santa Clarita, CA (US); Sung Jin Lee, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 117 days.

(21) Appl. No.: 16/603,868

(22) PCT Filed: Apr. 25, 2017

(86) PCT No.: PCT/US2017/029464
§ 371 (c)(1),
(2) Date: Oct. 9, 2019

(87) PCT Pub. No.: WO2018/199936
PCT Pub. Date: Nov. 1, 2018

(65) Prior Publication Data
US 2020/0114151 A1    Apr. 16, 2020

(51) Int. Cl.
*A61N 1/36*    (2006.01)
*A61N 1/08*    (2006.01)
*A61B 5/00*    (2006.01)
*A61N 1/372*    (2006.01)
*A61N 1/375*    (2006.01)

(52) U.S. Cl.
CPC ........ *A61N 1/36038* (2017.08); *A61B 5/0031* (2013.01); *A61N 1/086* (2017.08); *A61N 1/375* (2013.01); *A61N 1/37229* (2013.01)

(58) Field of Classification Search
CPC .............. A61N 1/0541; A61N 1/36038; A61N 1/36086; A61N 1/086; A61N 1/0031; A61N 1/37229; A61N 1/375; H04R 225/51
See application file for complete search history.

(56) References Cited

U.S. PATENT DOCUMENTS

| 4,214,366 A | 7/1980 | Laban |
| 4,352,960 A | 10/1982 | Dormer et al. |
| 4,595,390 A | 6/1986 | Hakim et al. |

(Continued)

FOREIGN PATENT DOCUMENTS

| EP | 2117489 B1 | 5/2010 |
| EP | 2853287 A1 | 4/2015 |

(Continued)

OTHER PUBLICATIONS

PCT International Search and Written Opinion dated Feb. 5, 2018 for PCT App. Ser. No. PCT/US2017/029464.

(Continued)

*Primary Examiner* — Mallika D Fairchild
*Assistant Examiner* — Minh Duc G Pham
(74) *Attorney, Agent, or Firm* — Henricks Slavin LLP

(57) ABSTRACT

A cochlear implant including a cochlear lead, an antenna, a stimulation processor, and a magnet apparatus, associated with the antenna, including a case and a magnet assembly, having a spine and at least one magnet that is secured to the spine, that is located within the case and is rotatable relative to the case.

19 Claims, 6 Drawing Sheets

(56) References Cited

U.S. PATENT DOCUMENTS

| | | |
|---|---|---|
| 4,606,329 A | 8/1986 | Hough |
| 4,612,915 A | 9/1986 | Hough et al. |
| 4,618,949 A | 10/1986 | Lister |
| RE32,947 E | 6/1989 | Dormer et al. |
| 5,290,281 A | 3/1994 | Tschakaloff |
| 5,755,762 A | 5/1998 | Bush |
| 5,824,022 A | 10/1998 | Zilberman et al. |
| 5,945,762 A | 8/1999 | Chen et al. |
| 6,032,677 A | 3/2000 | Blechman et al. |
| 6,178,353 B1 | 1/2001 | Griffith et al. |
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,461,288 B1 | 10/2002 | Holcomb |
| 6,599,321 B2 | 7/2003 | Hyde, Jr. |
| 6,838,963 B2 | 1/2005 | Zimmerling |
| 7,091,806 B2 | 8/2006 | Zimmerling et al. |
| 7,190,247 B2 | 3/2007 | Zimmerling |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B2 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 | 3/2018 | Lee |
| 9,931,501 B2 | 4/2018 | Smyth |
| 10,300,276 B2 | 5/2019 | Lee et al. |
| 10,463,849 B2 | 11/2019 | Lee et al. |
| 10,532,209 B2 | 1/2020 | Lee et al. |
| 10,646,712 B2 | 5/2020 | Smith et al. |
| 10,646,718 B2 | 5/2020 | Smith et al. |
| 10,806,936 B2 | 10/2020 | Crawford et al. |
| 10,821,279 B2 | 11/2020 | Lee et al. |
| 11,097,095 B2 | 8/2021 | Smith et al. |
| 11,287,495 B2 | 3/2022 | Smith et al. |
| 2004/0012470 A1 | 1/2004 | Zimmerling et al. |
| 2004/0059423 A1 | 3/2004 | Barnes et al. |
| 2004/0063072 A1 | 4/2004 | Honkura et al. |
| 2004/0210103 A1 | 10/2004 | Westerkull |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2006/0116743 A1 | 6/2006 | Gibson et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0097496 A1 | 4/2008 | Chang et al. |
| 2008/0103350 A1 | 5/2008 | Farone |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 | 9/2011 | Zimmerling et al. |
| 2011/0255731 A1 | 10/2011 | Ball |
| 2011/0264172 A1 | 10/2011 | Zimmerling et al. |
| 2012/0296155 A1* | 11/2012 | Ball .............. A61N 1/3718 607/57 |
| 2013/0079749 A1 | 3/2013 | Overstreet et al. |
| 2013/0150657 A1 | 6/2013 | Leigh et al. |
| 2013/0184804 A1 | 7/2013 | Dalton |
| 2013/0281764 A1 | 10/2013 | Bjorn et al. |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0336447 A1 | 11/2014 | Bjorn et al. |
| 2014/0343626 A1 | 11/2014 | Thenuwara et al. |
| 2015/0025613 A1 | 1/2015 | Nyberg, II et al. |
| 2015/0073205 A1 | 3/2015 | Ball et al. |
| 2015/0087892 A1* | 3/2015 | Tourrel .............. A61N 1/37518 607/57 |
| 2015/0094521 A1 | 4/2015 | Neuman et al. |
| 2015/0100109 A1 | 4/2015 | Feldman et al. |
| 2015/0265842 A1 | 9/2015 | Ridker |
| 2015/0320523 A1 | 11/2015 | Way et al. |
| 2015/0367126 A1 | 12/2015 | Smyth |
| 2015/0382114 A1 | 12/2015 | Andersson et al. |
| 2016/0008596 A1 | 1/2016 | Gibson et al. |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0213936 A1 | 7/2016 | Heerlein et al. |
| 2016/0310737 A1 | 10/2016 | Tourrel et al. |
| 2016/0361537 A1* | 12/2016 | Leigh .............. A61N 1/37518 |
| 2016/0381473 A1 | 12/2016 | Gustafsson |
| 2016/0381474 A1 | 12/2016 | Gustafsson et al. |
| 2017/0050027 A1 | 2/2017 | Andersson et al. |
| 2017/0078808 A1 | 3/2017 | Kennes |
| 2017/0156010 A1 | 6/2017 | Verma et al. |
| 2017/0239476 A1 | 8/2017 | Lee et al. |
| 2017/0347208 A1 | 11/2017 | Jurkiewicz |
| 2018/0028818 A1 | 2/2018 | Anderson et al. |
| 2018/0056084 A1 | 3/2018 | Alam |
| 2018/0110985 A1 | 4/2018 | Walter |
| 2018/0110986 A1 | 4/2018 | Lee |
| 2018/0133486 A1 | 5/2018 | Smith |
| 2018/0146308 A1 | 5/2018 | Leigh et al. |
| 2018/0160241 A1* | 6/2018 | Gustafsson .......... H04R 25/606 |
| 2018/0160242 A1 | 6/2018 | Sriskandarajah |
| 2018/0185634 A1 | 7/2018 | Smyth |
| 2018/0249262 A1 | 8/2018 | Santek |
| 2018/0270591 A1 | 9/2018 | Kennes |
| 2018/0296826 A1 | 10/2018 | Lee et al. |
| 2018/0303602 A1 | 10/2018 | Leigh |
| 2018/0304078 A1 | 10/2018 | Crawford et al. |
| 2018/0369586 A1* | 12/2018 | Lee .............. A61N 1/36038 |
| 2019/0015662 A1 | 1/2019 | Raje et al. |
| 2019/0046797 A1 | 2/2019 | Calixto et al. |

(56) References Cited

U.S. PATENT DOCUMENTS

| | | | |
|---|---|---|---|
| 2019/0053908 A1 | 2/2019 | Cook et al. |
| 2019/0076649 A1 | 3/2019 | Lee et al. |
| 2019/0255316 A1 | 8/2019 | Lee et al. |
| 2019/0298417 A1 | 10/2019 | Barrett et al. |
| 2020/0230422 A1 | 7/2020 | Gibson et al. |
| 2020/0238088 A1 | 7/2020 | Smith et al. |
| 2020/0330777 A1 | 10/2020 | Smith et al. |
| 2020/0391023 A1 | 12/2020 | Lee et al. |
| 2021/0046311 A1 | 2/2021 | Brehm et al. |
| 2021/0106815 A1 | 4/2021 | Smith et al. |
| 2021/0156934 A1 | 5/2021 | Smith et al. |
| 2021/0299456 A1 | 9/2021 | Smith et al. |
| 2021/0316136 A1 | 10/2021 | Smith et al. |
| 2021/0339021 A1 | 11/2021 | Brehm et al. |

FOREIGN PATENT DOCUMENTS

| | | | |
|---|---|---|---|
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016190886 A1 | 12/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |
| WO | WO2017105604 A1 | 6/2017 |
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |
| WO | WO2018217187 A1 | 11/2018 |
| WO | WO2019083540 A1 | 5/2019 |
| WO | WO2019160555 A1 | 8/2019 |
| WO | WO2020092185 A1 | 5/2020 |
| WO | WO2021201845 A1 | 10/2021 |

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.
Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.
U.S. Appl. No. 16/852,457, filed Apr. 28, 2020, 20200238088 A1.
U.S. Appl. No. 16/499,311, filed Sep. 29, 2019.
U.S. Appl. No. 16/754,126, filed Apr. 6, 2020.
U.S. Appl. No. 16/966,885, filed Aug. 1, 2020.
U.S. Appl. No. 17/073,322, filed Oct. 17, 2020.
U.S. Appl. No. 17/008,291, filed Aug. 31, 2020, 20200391023 A1.
U.S. Appl. No. 16/499,311, filed Sep. 29, 2019, 20210106815 A1.
U.S. Appl. No. 17/355,225, filed Jun. 23, 2021.
U.S. Appl. No. 17/335,161, filed Jun. 1, 2021.
U.S. Appl. No. 17/346,343, filed Jun. 14, 2021.
U.S. Appl. No. 15/568,469, filed Oct. 21, 2017, 20180110985 A1.
U.S. Appl. No. 15/770,207, filed Apr. 22, 2018, U.S. Pat. No. 10,806,936.
U.S. Appl. No. 17/073,322, filed Oct. 17, 2020, 20210170167 A1.
U.S. Appl. No. 16/060,383, filed Jun. 7, 2018, U.S. Pat. No. 10,532,209.
U.S. Appl. No. 15/591,054, filed May 9, 2017, U.S. Pat. No. 9,919,154.
U.S. Appl. No. 16/009,600, filed Jun. 15, 2018, U.S. Pat. No. 10,821,279.
U.S. Appl. No. 16/403,582, filed May 5, 2019, U.S. Pat. No. 10,463,849.
U.S. Appl. No. 17/008,291, filed Aur. 31, 2020, 20200391023 A1.
U.S. Appl. No. 16/610,502, filed Nov. 2, 2019, 20210156934 A1.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 15/703,808, filed Sep. 13, 2017, U.S. Pat. No. 10,646,712.
U.S. Appl. No. 15/805,025, filed Nov. 6, 2017, U.S. Pat. No. 10,646,718.
U.S. Appl. No. 16/852,457, filed Apr. 18, 2020, 20200238088 A1.
U.S. Appl. No. 16/499,311, filed Sep. 29, 2019, U.S. Pat. No. 11,097,095.
U.S. Appl. No. 17/355,225, filed Jun. 23, 2021, 20210316136 A1.
U.S. Appl. No. 16/603,868, filed Oct. 9, 2019, 20200114151 A1.
U.S. Appl. No. 16/754,126, filed Apr. 6, 2020, 20200330777 A1.
U.S. Appl. No. 17/335,161, filed Jun. 1, 2021, 20210339021 A1.
U.S. Appl. No. 17/346,343, filed Jun. 14, 2021, 20210299456 A1.
U.S. Appl. No. 17/499,813, filed Oct. 12, 2021.

* cited by examiner

COCHLEAR IMPLANTS HAVING IMPACT RESISTANT MRI-COMPATIBLE MAGNET APPARATUS

CROSS-REFERENCE TO RELATED APPLICATIONS

This application is the U.S. National Stage of PCT App. Ser. No. PCT/US2017/029464, filed Apr. 25, 2017.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics Harmony™ BTE sound processor, the Advanced Bionics Naida CI Q Series BTE sound processors and the Advanced Bionics Neptune™ body worn sound processor.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing. The skin and subcutaneous tissue that separates the headpiece magnet and implant magnet is sometimes referred to as the "skin flap," which is frequently 3 mm to 10 mm thick.

The magnitude of the retention force between the headpiece magnet and implant magnet is an important aspect of an ICS system. If the force is too low, the headpiece will not remain in place on the head during typical activities. If, on the other hand, the force is too high, the pressure on the skin flap can result is discomfort and tissue necrosis. The magnitude of the retention force is dictated by the strength of the magnets and the distance between the magnets, which is a function of the thickness of the skin flap. The strength of the headpiece magnet is frequently selected during the post-implantation headpiece fitting processes.

The present inventors have determined that conventional cochlear implants are susceptible to improvement. For example, the magnets in many conventional cochlear implants are disk-shaped and have north and south magnetic dipoles that are aligned in the axial direction of the disk. Such magnets are not compatible with magnetic resonance imaging ("MRI") systems. In particular, the cochlear implant 10 illustrated in FIG. 1 includes, among other things, a housing 12 and a disk-shaped solid block magnet 14. The implant magnet produces a magnetic field M in a direction that is perpendicular to the patient's skin and parallel to the axis A, and this magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may demagnetize the implant magnet 14 or generate a significant amount of torque T on the implant magnet 14. The torque T may dislodge the implant magnet 14 from the pocket within the housing 12, reverse the magnet 14 and/or dislocate the cochlear implant 10, all of which may also induce tissue damage.

One proposed solution involves surgically removing the implant magnet 14 prior to the MRI procedure and then surgically replacing the implant magnet thereafter. The present inventor has determined that removal and reinsertion can be problematic because some patients will have many MRI procedures during their lifetimes, and repeated surgeries can result in skin necrosis at the implant site.

Another proposed solution involves the use of rotatable magnets. Referring to FIGS. 2 and 3, the cochlear implant 18 includes an implant housing 20 and a magnet apparatus 22. The magnet apparatus 22 includes a diametrically magnetized disk-shaped magnet 24 that is located within, and is rotatable relative to, a hermetically sealed case 26. The magnet 24, which rotates relative to the implant housing 20 and case 26 about an axis A, has a N-S orientation that is perpendicular to the axis A. The associated external headpiece 28 includes a diametrically magnetized disk-shaped magnet 30 that is not rotatable relative to the remainder of the headpiece. The implanted magnet 24 is able to rotate about the axis A into alignment with the external magnet 30, and is also able to rotate about the axis A into alignment with an MRI magnetic field that is perpendicular to the axis A.

Although the cochlear implant illustrated in FIGS. 2 and 3 represents an advance in the art, the present inventors have determined that it is susceptible to improvement. For example, the magnet apparatus 22 may be subjected to impact forces IF (e.g., when the user bumps his or her head) that will fracture the magnet 24 and/or inwardly deform the case 26 to the point at which plastic (or "permanent") deformation occurs. The fracturing of the magnet may create magnetic material particles that with interfere with magnet rotation and the rotational interference may in turn lead to the creation of additional magnetic material particles when the fractured magnet is subjected to MRI-generated torque.

The magnetic attraction of a fractured magnet is also less than that of an intact magnet, which may result in the fractured magnet being unable to maintain the associated headpiece on the user's head. A permanently inwardly deformed case may pinch the magnet and interfere with rotation. In either instance, the ability of the magnet 24 to rotate into alignment with the external headpiece magnet 30 or an MRI magnetic field will be compromised.

SUMMARY

A cochlear implant in accordance with one of the present inventions may include a cochlear lead, an antenna, a stimulation processor, and a magnet apparatus, associated with the antenna, including a case and a magnet assembly, having a spine and at least one magnet that is secured to the spine, that is located within the case and is rotatable relative to the case. A system in accordance with one of the present inventions includes such a cochlear implant and a headpiece.

There are a number of advantages associated with such apparatus and systems. For example, the spine protects the at least one magnet from impacts forces that could damage the at least one magnet and impair rotation.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

Figure 1:
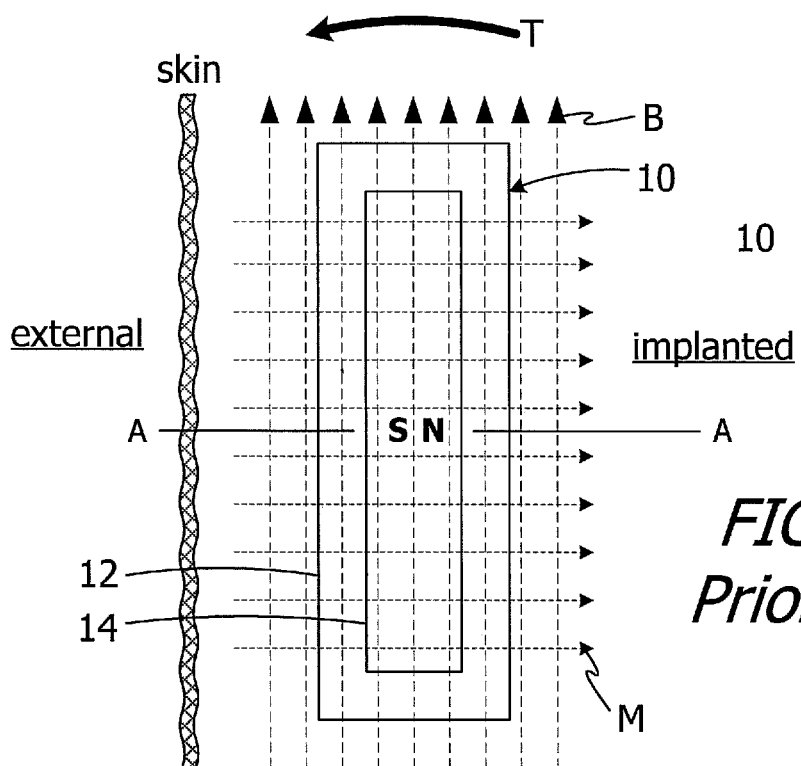
FIG. 1 is a diagrammatic view showing a conventional cochlear implant in an MRI magnetic field.
Figure 2:
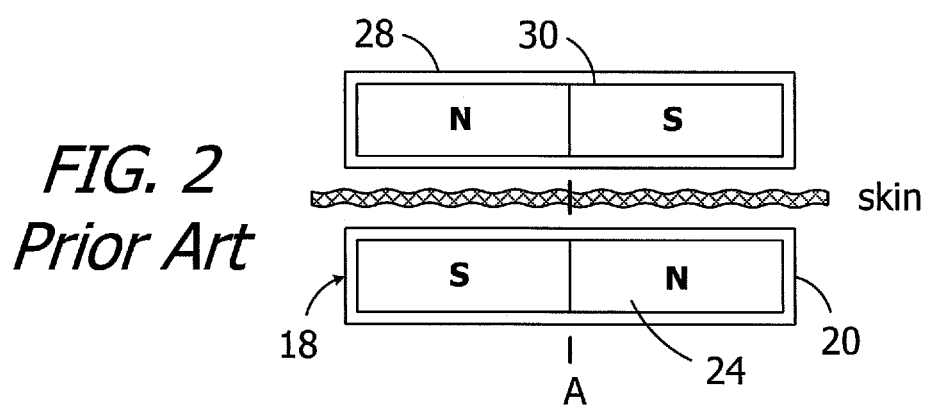
FIG. 2 is a diagrammatic view of a conventional implant and external headpiece.
Figure 3:
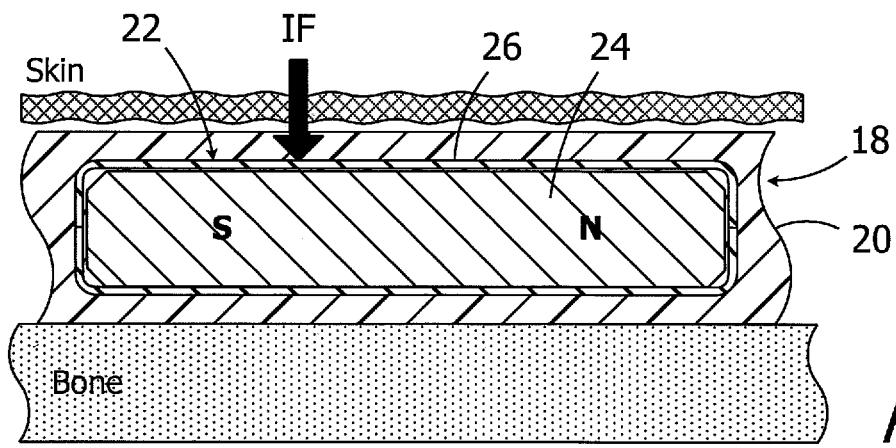
FIG. 3 is a section view of a conventional implant magnet apparatus.
Figure 4:
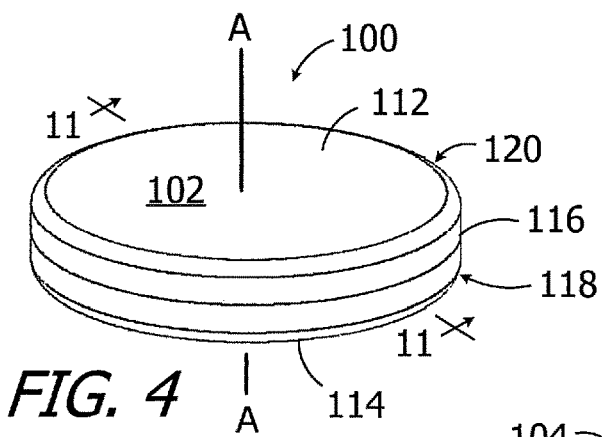
FIG. 4 is a perspective view of an implant magnet apparatus in accordance with one embodiment of a present invention.
Figure 5:
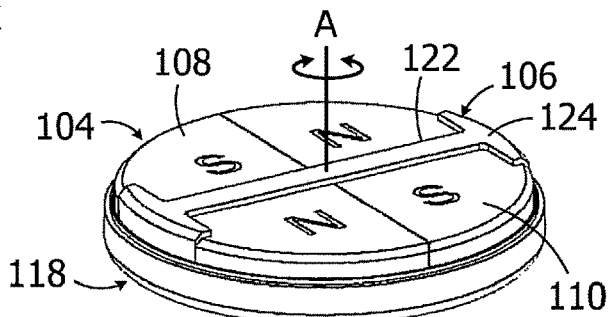
FIG. 5 is a perspective view of a portion of the implant magnet apparatus illustrated in FIG. 4.
Figure 6:
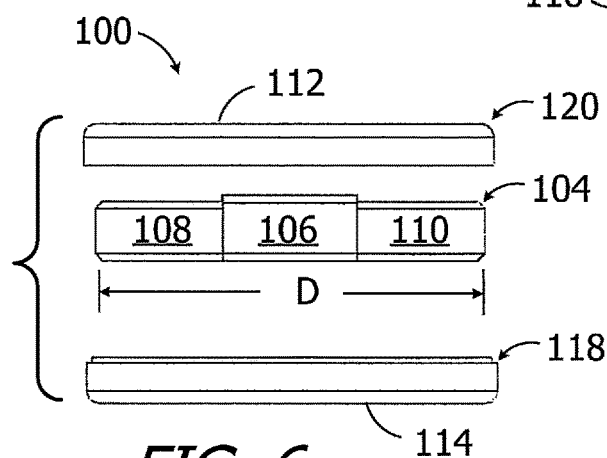
FIG. 6 is an exploded view of the implant magnet apparatus illustrated in FIG. 4.
Figure 7:
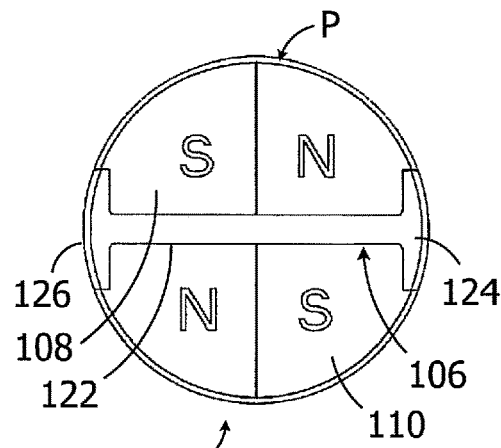
FIG. 7 is a top view of a portion of the implant magnet apparatus illustrated in FIG. 4.

The following is a detailed description of the best presently known modes of carrying out the inventions. This description is not to be taken in a limiting sense, but is made merely for the purpose of illustrating the general principles of the inventions.

As illustrated for example in FIGS. 4-9, an exemplary magnet apparatus 100 includes a disk-shaped case 102 and a magnet assembly 104. An axis A is defined by both the case 102 and the magnet assembly 104. The magnet assembly 104 is freely rotatable (over 360°) about the axis A relative to the case 102. As used herein, the phrase "freely rotatable about an axis" refers to an object that can rotate about an axis relative to an adjacent object, albeit with some friction between the two objects, without mechanical limitation of the rotation (e.g., with a stop or biasing device that opposes the rotation). The magnet assembly 104 includes at least one magnet and a spine 106 that protects the magnet in the manner described below. In the illustrated embodiment, first and second magnets 108 and 110 are located on opposite sides of the spine. The first and second magnets 108 and 110 rotate with the spine 106 within the case 102, and are not rotatable relative to the spine.

The exemplary case 102 is not limited to any particular configuration, size or shape. In the illustrated implementation, the exemplary case 102 includes a top wall 112, a bottom wall 114, and a cylindrical side wall 116 between the top and bottom walls. As used herein, the word "top" refers to a structure or surface that, post implantation, faces the skin and (if present) the associated headpiece, and the word "bottom" refers to a structure or surface that, post implantation, faces bone. In the illustrated implementation, the case 102 is assembled from a base 118 that includes the bottom wall 114 and a portion of the side wall 116, and a cover 120 that includes the top wall 112 and another portion of the side wall 116. The base 118 and the cover 120 may be secured to one another in such a manner that a hermetic seal is formed between the cover and the base. Suitable techniques for securing the cover 120 to the base 118 include, for example, seam welding with a laser welder.

Figure 8A:
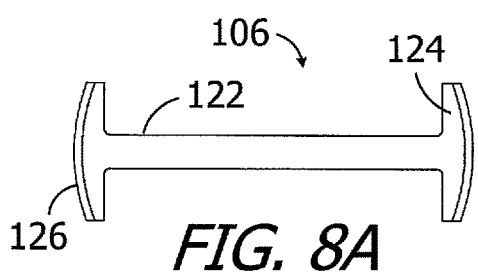
FIG. 8A is a top view of a portion of the implant magnet apparatus illustrated in FIG. 4.
Figure 8B:
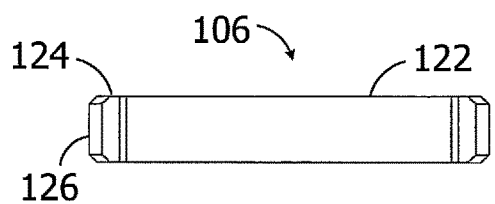
FIG. 8B is a side view of a portion of the implant magnet apparatus illustrated in FIG. 4.

Turning to the exemplary magnet assembly 104, and although the spine is not limited to any particular shape, the exemplary spine 106 has a shape similar to an "I" beam and includes a web 122 and a pair of flanges 124 with curved outer surfaces 126 (FIGS. 8A and 8B). The spine 106 protects the magnets 108 and 110 from impact forces in the manner discussed below with reference to FIGS. 12 and 13 and also acts as a rotational beam. The spine 106 lies on, and has a length equal to, the diameter D of the magnet assembly 104. The exemplary magnets 108 and 110, which may be secured to the spine 106 with adhesive or other suitable instrumentalities, are linearly magnetized and are oriented in such a manner that the N-S axis of each magnet is parallel to the diameter D of the magnet assembly 104 and to the spine web 122. The N and S poles of magnet 108 are respectively aligned with the S and N poles of magnet 110 in directions perpendicular to the spine web 122 (FIG. 7) to define the exemplary 4-pole magnet assembly 104. Other exemplary spines and magnets are described below with reference to FIGS. 17-22.

Figure 9:
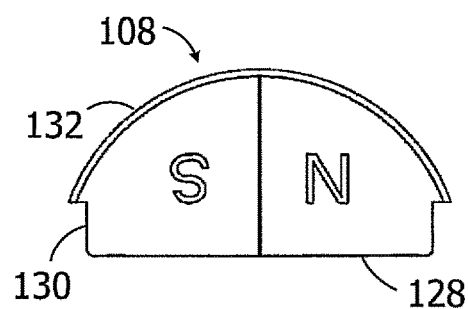
FIG. 9 is a top view of a portion of the implant magnet apparatus illustrated in FIG. 4.

Referring to FIG. 9, each magnet 108 and 110 includes an end wall 128 that abuts the spine web 122, a pair of indentations 130 that receive a portion of the spine flanges 124, and a curved outer surface 132. The outer surfaces 126 and 132 of the spine 106 and the magnets 108 and 110 form the perimeter P of the magnet assembly 104.

Figure 10:
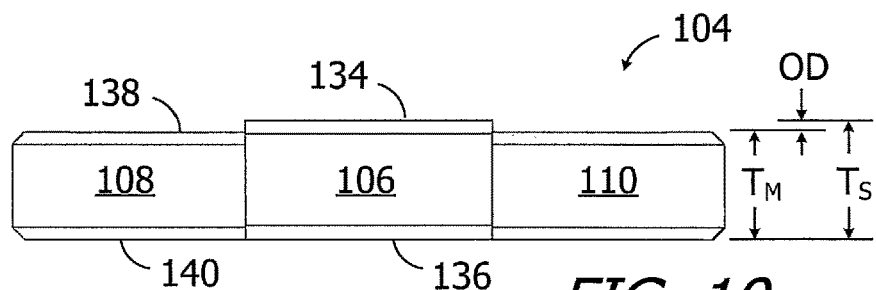
FIG. 10 is a side view of a portion of the implant magnet apparatus illustrated in FIG. 4.
Figure 11:
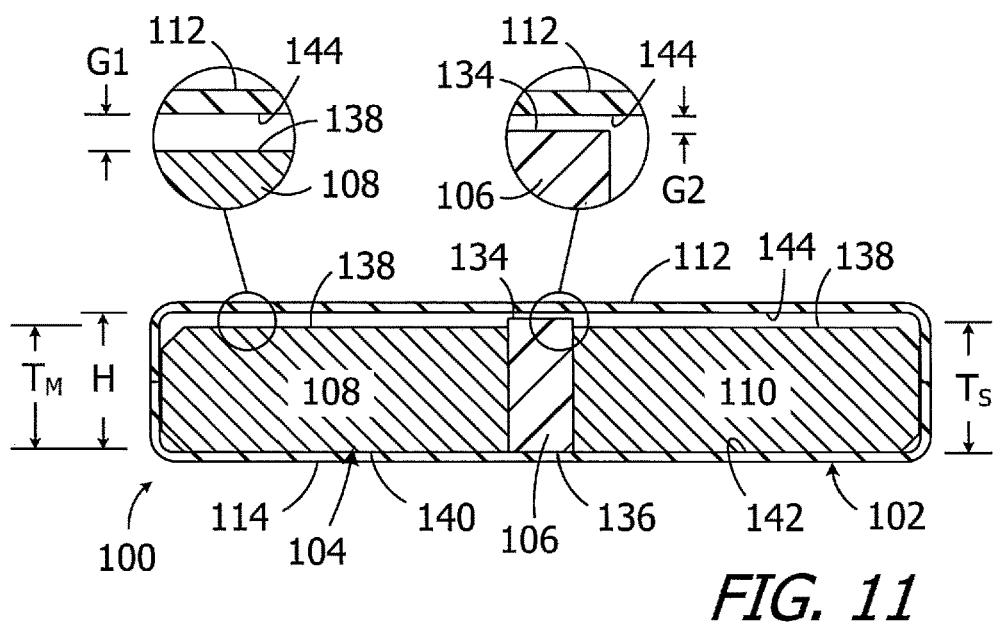
FIG. 11 is a section view taken along line 11-11 in FIG. 4.

Referring to FIG. 10, the spine 106 has top and bottom surfaces 134 and 136 and the magnets 108 and 110 have top and bottom surfaces 138 and 140. The magnet thickness $T_M$ is less than the spine thickness $T_S$, and the bottom surfaces 136 and 140 of the spine 106 and magnets 108 and 110 are aligned with one another. As a result, the top surfaces 134 and 138 of the spine 106 and magnets 108 and 110 are offset by an offset distance OD. Put another way, the spine 106 extends beyond the top surface 138 of the magnets 108 and 110 by the offset distance OD. Turning to FIG. 11, the case 102 has an internal volume with a height H defined by the distance between the inner surfaces 142 and 144 of the bottom and top walls 114 and 112. The magnet thickness $T_M$ is less than the height H of the internal volume of the case 102, as is the spine thickness $T_S$, and the bottom surfaces 138 and 140 of the spine 106 and magnets 108 and 110 abut the inner surface 142 of the case bottom wall 114. There is, therefore, a gap G1 between the top surfaces 138 of the magnets 108 and 110 and the inner surface 144 of the case top wall 112. There is also a smaller gap G2 between the top surface 134 of the spine 106 and the inner surface 144 of the case top wall 112. In other instances, the spine thickness $T_S$ may be essentially the same as the height H of the internal volume of the case 102, thereby eliminating the gap G2.

Figure 12:
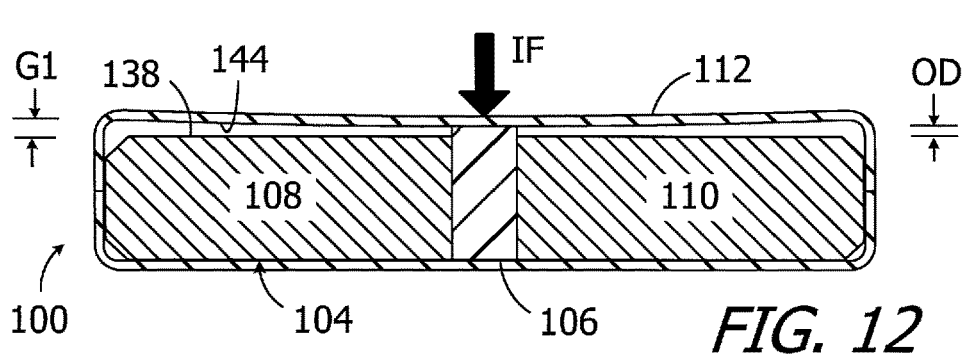
FIG. 12 is a section view showing the implant magnet apparatus illustrated in FIG. 4 being subjected to an impact force.
Figure 13:
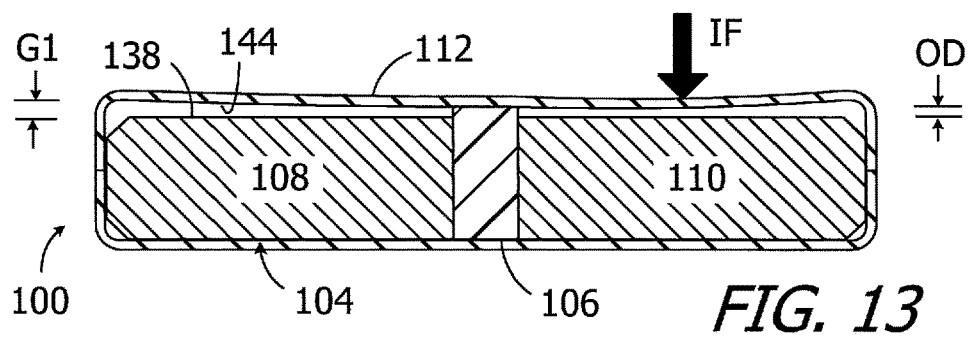
FIG. 13 is a section view showing the implant magnet apparatus illustrated in FIG. 4 being subjected to an impact force.

The spine 106 protects the magnets 108 and 110, especially those formed from somewhat brittle sintered materials, from impact forces that act on the exterior surface of case 102. For example, in those instances where impact forces IF are aligned with any portion of the spine 106 (i.e., the web 122 or the flanges 124) and are of sufficient magnitude to bend the top wall 112 of the case 102, the inner surface 144 will at most contact the spine. The inner surface 144 of the top wall 112 will not come into contact with the magnets 108 and 110, as shown in FIG. 12. The gap G2 may be eliminated by deflection of the top wall 112, but the gap G1 will be at most reduced slightly. Thus, the spine 106 prevents damage to the magnets.

In those instances where the impact forces IF on the case top wall 112 are not aligned with any portion of the spine 106 (FIG. 13), and are instead located somewhere between the spine and the cylindrical side wall 116, the spine will nevertheless support a portion (or portions) of the deflected top wall 112. The spine 106 and case side wall 116 will act as supports for the deflected top wall 112, thereby decreasing the distance between the supports as compared to a conventional magnet assembly where top wall is only supported at the outer perimeter by the case side wall. As a result of the decreased distance between the supports, the deflection of the of top wall 112 beyond that which result in the top wall touching the spine 106 will be far less for a given impact force IF, as compared to an otherwise identical magnet apparatus without the spine.

It should also be noted that regardless of whether or not the impact forces IF are aligned with the spine 106, deformation of the case top wall 112 will not reach the point at which plastic (or "permanent") deformation occurs. Rather, the deformation will remain within the elastic (or "temporary") range and the case top wall 112 will return to its original shape when the impact force IF is removed.

With respect to materials, the case 102 and the spine 106 may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE), ultra-high-molecular-weight polyethylene (UHMWPE), polytetrafluoroethylene (PTFE) and polyamide. In particular, exemplary metals include commercially pure titanium (e.g., Grade 2) and the titanium alloy Ti-6Al-4V (Grade 5), while exemplary metal thicknesses of the case 102 may range from 0.20 mm to 0.25 mm. The magnets 108 and 110 may be formed from sintered materials such as, but not limited to, neodymium-iron-boron ($Nd_2Fe_{14}B$), isotropic neodymium, anisotropic neodymium, and samarium-cobalt ($Sm_2Co_{17}$), which have relatively high magnetic strength, but can be somewhat brittle. The magnets 108 and 110 may be stable magnets that are magnetized prior to assembly. In other instances, such as the magnet assemblies 104d and 104e described below with reference to FIGS. 20 and 22, the magnets may be unstable and magnetized after being secured to the spine.

With respect to size and shape, the case 102 may have an overall size and shape similar to that of conventional cochlear implant magnets so that the magnet apparatus 100 can be substituted for a conventional magnet in an otherwise conventional cochlear implant. In some implementations, the outer diameter that may range from about 9 mm to about 16 mm and the outer thickness may range from about 2.3 mm to about 2.7 mm. In the context of the present magnet apparatus, the word "about" means +/−8%. The height H (FIG. 11) of the case internal volume may range from about 1.9 mm to about 2.3 mm. The diameter of the magnet apparatus 104, which will be slightly less than the inner diameter of the case 102, may range from about 11.5 mm to about 12.0 mm. The magnet thickness $T_M$ may range from about 1.6 mm to about 2.0 mm, while the spine thickness $T_S$ may range from about 2.1 mm to about 2.2 mm. So configured, the gap G1 may range from about 0.2 mm to about 0.25 mm, while the gap G2 may range from about 0.05 mm to about 0.15 mm. In the illustrated implementation, the diameter of the case 102 is about 12.65 mm, the thickness is about 2.5 mm, and the volume height H is about 2.1 mm. Turning to the magnet assembly 104 in the illustrated implementation, the diameter is about 12.0 mm, the magnet thickness $T_M$ is about 1.8 mm, and the spine thickness $T_S$ is about 2.0 mm.

Figure 14:
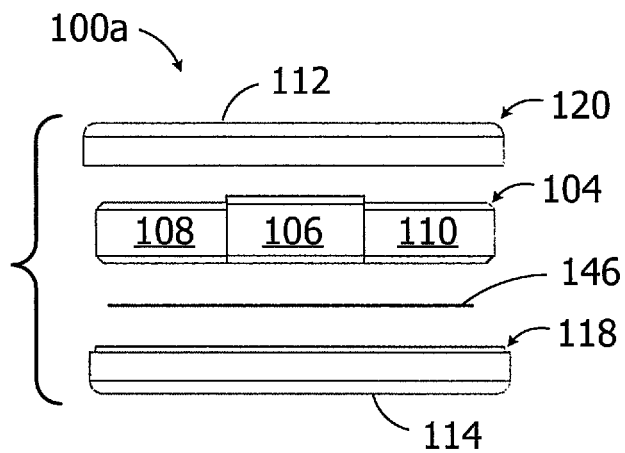
FIG. 14 is an exploded view of an implant magnet apparatus in accordance with one embodiment of a present invention.
Figure 15:
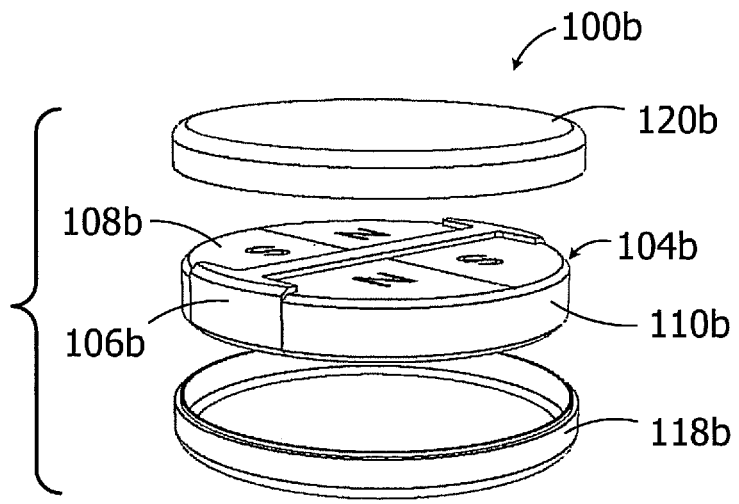
FIG. 15 is an exploded view of an implant magnet apparatus in accordance with one embodiment of a present invention.
Figures 16A, 16B:
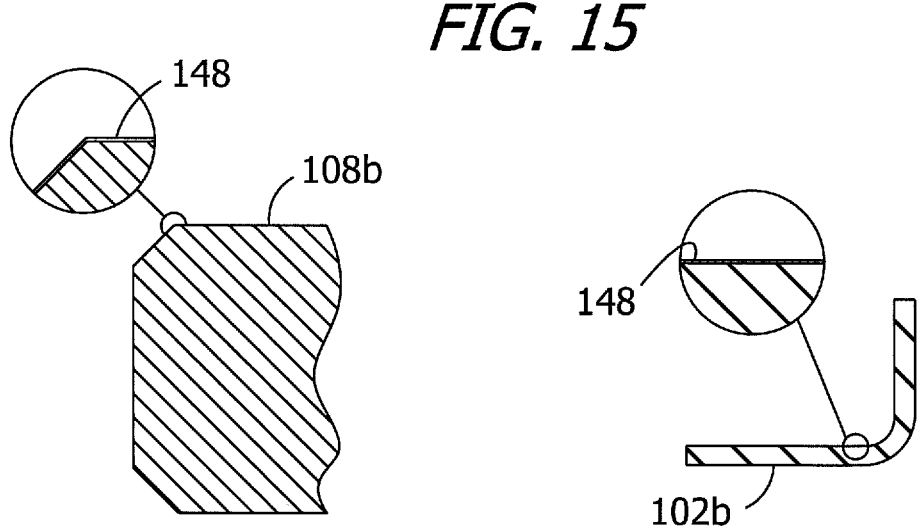
FIG. 16A is a section view of a portion of the implant magnet apparatus illustrated in FIG. 15.
FIG. 16B is a section view of a portion of the implant magnet apparatus illustrated in FIG. 15.

To facilitate rotation of the magnet assembly 104, lubricious friction reducing material may be provided between the case 102 and the magnet assembly. For example, the magnet apparatus 100a illustrated in FIG. 14 is substantially similar to the magnet apparatus 100 and similar elements are represented by similar reference numerals. Here, however, a lubricious disk 146 formed from PTFE, a hard material (e.g. titanium) with a lubricious coating, or other suitable materials, is positioned between the magnet assembly 104 and the case bottom wall 114. In other implementations (not shown), a pair of lubricious disks and a lubricious ring may be positioned between the case 102 and the magnet assembly 104. Alternatively, a lubricious layer may be added to the inner surface of the case and/or some or all of the various surfaces of the magnet assembly. The lubricious layer may be in the form of a specific finish of the inner surface that reduces friction, as compared to an unfinished surface, or may be a coating of a lubricious material such as diamond-like carbon (DLC), titanium nitride (TiN), PTFE, polyethylene glycol (PEG), Parylene, fluorinated ethylene propylene (FEP) and electroless nickel sold under the tradenames Nedox® and Nedox PF™. A DLC coating, for example, may be only 0.5 to 5 microns thick. To that end, the magnet apparatus 100b illustrated in FIGS. 15-16B is substantially similar to the magnet apparatus 100 and similar elements are represented by similar reference numerals. Here, however, the magnet apparatus 104b includes a lubricious layer 148 that covers the spine 106b as well as the magnets 108b and 110b. Alternatively, or in addition, the inner surface of the case 102b (i.e., the inner surfaces of the base 118b and cover 120b) may include a lubricious layer 148. In those instances where the base 118b and a cover 120b are formed by stamping, the finishing process may occur prior to stamping. Micro-balls, biocompatible oils and lubricating powders may also be added to the interior of the case 102 to reduce friction.

Figure 17:
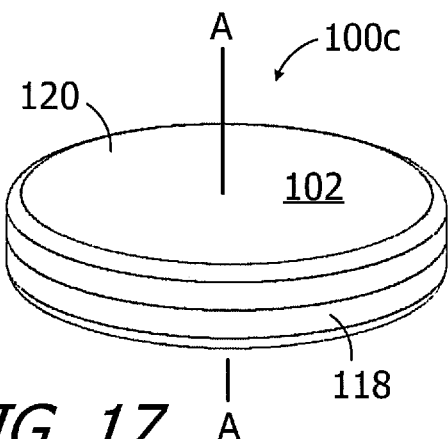
FIG. 17 is a perspective view of an implant magnet apparatus in accordance with one embodiment of a present invention.
Figure 18:
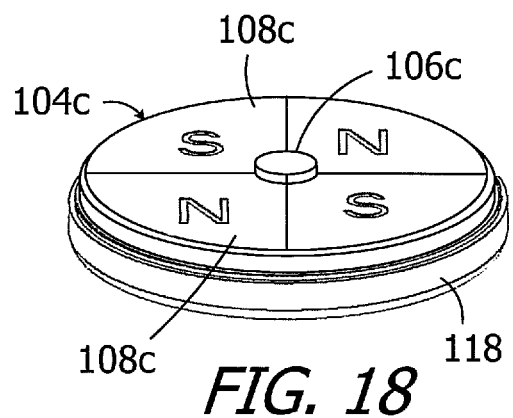
FIG. 18 is a perspective view of a portion of the implant magnet apparatus illustrated in FIG. 17.
Figure 19:
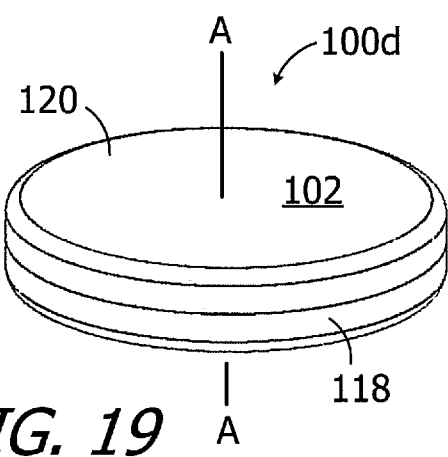
FIG. 19 is a perspective view of an implant magnet apparatus in accordance with one embodiment of a present invention.
Figure 20:
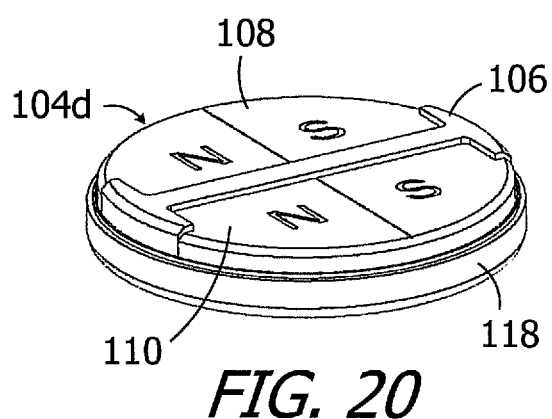
FIG. 20 is a perspective view of a portion of the implant magnet apparatus illustrated in FIG. 19.
Figure 21:
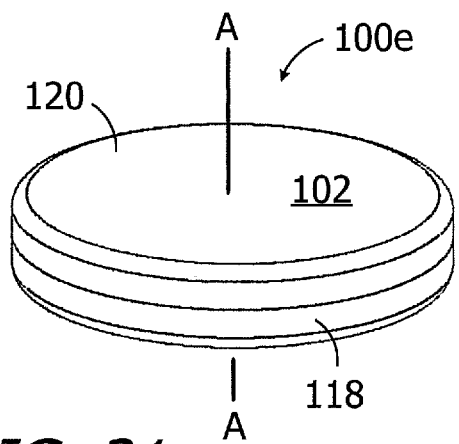
FIG. 21 is a perspective view of an implant magnet apparatus in accordance with one embodiment of a present invention.
Figure 22:
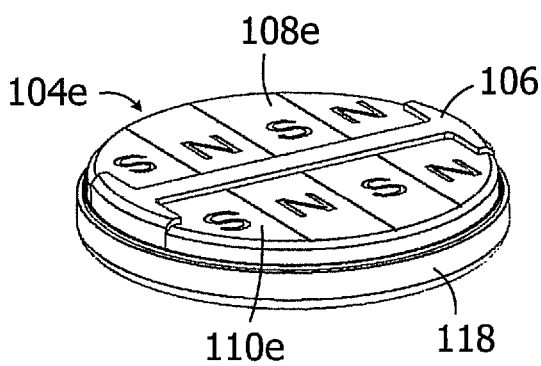
FIG. 22 is a perspective view of a portion of the implant magnet apparatus illustrated in FIG. 21.

Other exemplary magnet apparatus, which include magnet assemblies with spines, are illustrated in FIGS. 17-20. The magnet apparatus 100c illustrated in FIGS. 17 and 18 is substantially similar to the magnet apparatus 100 and similar elements are represented by similar reference numerals. Here, however, the spine 106c in the magnet assembly 104c is in the form of a cylindrical post that is located on the axis A, and the magnets 108c and 108d abut one another. The magnet apparatus 100d illustrated in FIGS. 19 and 20 is substantially similar to the magnet apparatus 100 and similar elements are represented by similar reference numerals. Here, however, the orientation of the magnet 108 in magnet assembly 104d is reversed as compared to the magnet 108 in magnet assembly 104 (FIG. 5), which may result in a decrease in MRI-generated torque and an increase in headpiece misalignment. Turning to FIGS. 21 and 22, the magnet apparatus 100e is substantially similar to the magnet apparatus 100 and similar elements are represented by similar reference numerals. Here, however, the magnet assembly 104e includes a pair of magnets 108e and a pair of magnets 110e in respective Halbach arrays which, as compared to the magnet assembly 104 (FIG. 5), may result in stronger magnet attraction to the associated headpiece magnet. The magnet apparatus 100c-100e may also include lubricious friction reducing material such as that described above with reference to FIGS. 14-16B.

Figure 23:
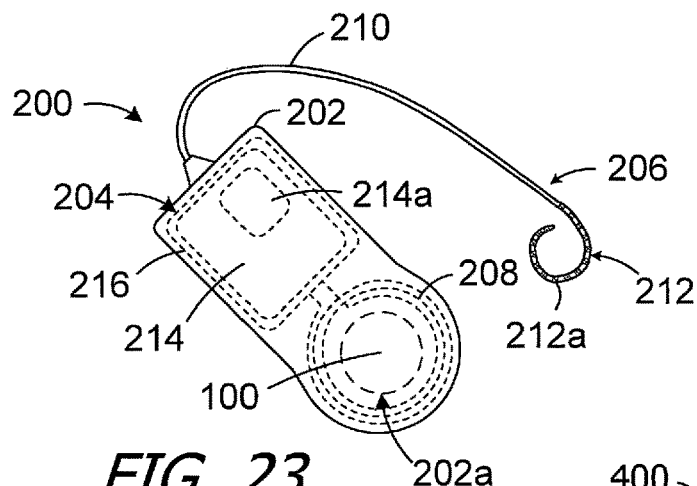
FIG. 23 is a plan view of a cochlear implant in accordance with one embodiment of a present invention.

One example of a cochlear implant (or "implantable cochlear stimulator") including the present magnet apparatus 100 (or 100a-100e) is the cochlear implant 200 illustrated in FIG. 23. The cochlear implant 200 includes a flexible housing 202 formed from a silicone elastomer or other suitable material, a processor assembly 204, a cochlear lead 206, and an antenna 208 that may be used to receive data and power by way of an external antenna that is associated with, for example, a sound processor unit. The cochlear lead 206 may include a flexible body 210, an electrode array 212 at one end of the flexible body, and a plurality of wires (not shown) that extend through the flexible body from the electrodes 212a (e.g., platinum electrodes) in the array 212 to the other end of the flexible body. The magnet apparatus 100 is located within a region encircled by the antenna 208 (e.g., within an internal pocket 202a defined by the housing 202) and insures that an external antenna (discussed below) will be properly positioned relative to the antenna 208. The exemplary processor assembly 204, which is connected to the electrode array 212 and antenna 208, includes a printed circuit board 214 with a stimulation processor 214a that is located within a hermetically sealed case 216. The stimulation processor 214a converts the stimulation data into stimulation signals that stimulate the electrodes 212a of the electrode array 212.

Figure 24:
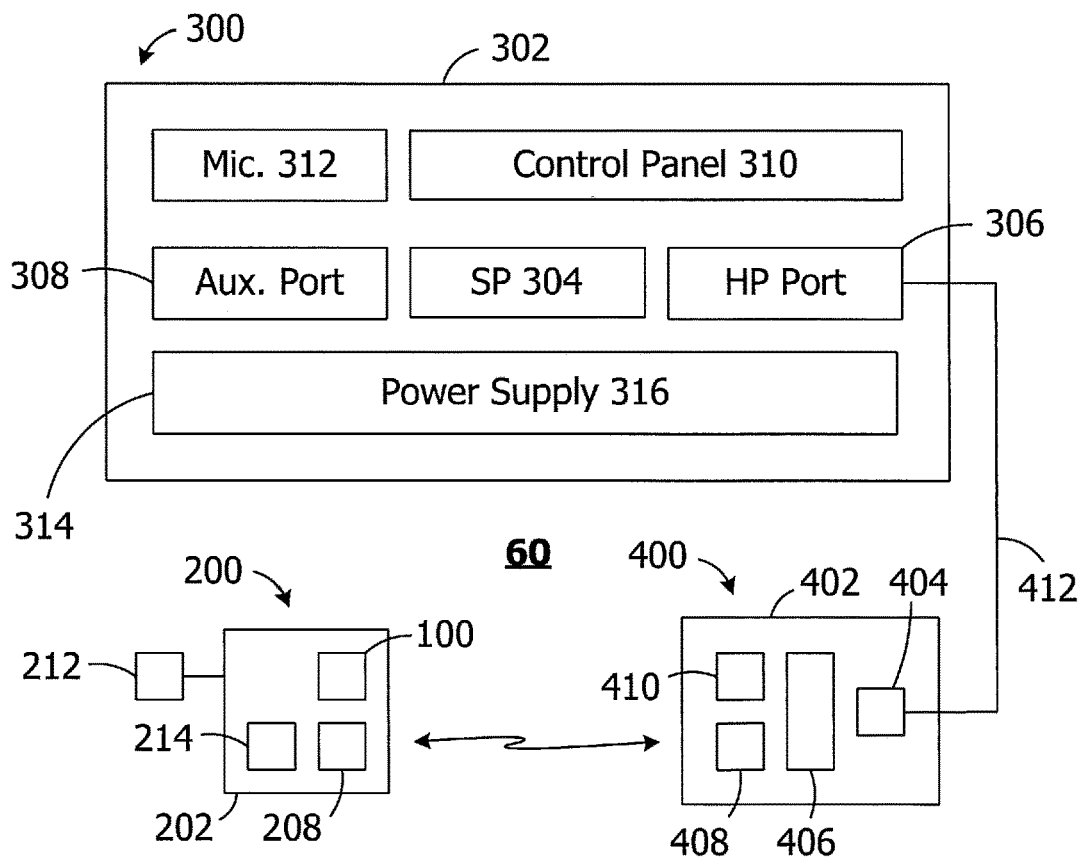
FIG. 24 is a block diagram of a cochlear implant system in accordance with one embodiment of a present invention.

Turning to FIG. 24, the exemplary cochlear implant system 60 includes the cochlear implant 200, a sound processor, such as the illustrated body worn sound processor 300 or a behind-the-ear sound processor, and a headpiece 400.

The exemplary body worn sound processor 300 in the exemplary ICS system 60 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data. The exemplary headpiece 400 includes a housing 402 and various components, e.g., a RF connector 404, a microphone 406, an antenna (or other transmitter) 408 and a disk-shaped positioning magnet 410, that are carried by the housing. The headpiece 400 may be connected to the sound processor headpiece port 306 by a cable 412. The positioning magnet 410 is attracted to the magnet apparatus 100 of the cochlear stimulator 200, thereby aligning the antenna 408 with the antenna 208.

Figure 25:
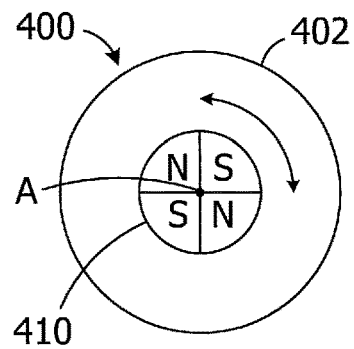
FIG. 25 is a diagrammatic view of a cochlear implant headpiece.

In at least some implementations, the headpiece positioning magnet 410 will be complementary to the implant magnet apparatus 100 (or 100a-100e). For example, because the volume of magnet material in the magnet apparatus may be reduced due to presence of the spine 106, as compared to a similarly sized conventional magnet apparatus which lacks a spine, the strength of the positioning magnet 410 may be increased, as compared to that of a positioning magnet intended for use with similarly sized conventional magnet apparatus. The positioning magnet 410 may also be freely rotatable (over 360°) about an axis A relative to the housing 402 and antenna 408, and have N-S orientations corresponding to that of the implant magnet apparatus 100 (or 100a-100e), as shown in FIG. 25.

The stimulation data and, in many instances power, is supplied to the headpiece 400. The headpiece 400 transcutaneously transmits the stimulation data, and in many instances power, to the cochlear implant 200 by way of a wireless link between the antennae. The stimulation processor 214*a* converts the stimulation data into stimulation signals that stimulate the electrodes 212*a* of the electrode array 212.

In at least some implementations, the cable 412 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the microphone 406 may be also be omitted in some instances. The functionality of the sound processor 300 and headpiece 400 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. The inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant, comprising:
   a cochlear lead including a plurality of electrodes;
   an antenna;
   a stimulation processor operably connected to the antenna and to the cochlear lead; and
   a magnet apparatus associated with the antenna and including a case and a magnet assembly located within the case, the case having a top wall and a bottom wall and defining an axis that passes through the top wall and the bottom wall, the magnet assembly having a spine and at least one magnet that is secured to the spine and is not rotatable relative to the spine such that the spine and the at least one magnet are rotatable together about the axis and relative to the case.

2. A cochlear implant as claimed in claim 1, wherein the case includes an internal volume defining a height;
   the at least one magnet defines a magnet thickness that is less than the internal volume height; and
   the spine defines a spine thickness that is greater than the magnet thickness.

3. A cochlear implant as claimed in claim 2, wherein the spine thickness is less than the internal volume height.

4. A cochlear implant as claimed in claim 1, wherein the magnet assembly defines a diameter; and
   the spine defines a length that is equal to the magnet assembly diameter.

5. A cochlear implant as claimed in claim 1, wherein the case includes a top internal surface and a bottom internal surface;
   the spine and the at least one magnet include respective top and bottom surfaces;
   the top surfaces of the spine and the at least one magnet are offset from one another; and
   the bottom surfaces of the spine and the at least one magnet are aligned with one another.

6. A cochlear implant as claimed in claim 1, wherein the at least one magnet comprises first and second magnets on opposite sides of the spine.

7. A cochlear implant as claimed in claim 6, wherein the first and second magnets each define a N-S axis that is parallel to the magnet assembly diameter.

8. A cochlear implant as claimed in claim 7, wherein the N and S poles of the first magnet are respectively aligned with the S and N poles of the second magnet.

9. A cochlear implant as claimed in claim 7, wherein the N and S poles of the first magnet are respectively aligned with the N and S poles of the second magnet.

10. A cochlear implant as claimed in claim 1, wherein the spine comprises a cylindrical post.

11. A cochlear implant as claimed in claim 1, further comprising:
    lubricious material between the case and the magnet assembly.

12. A cochlear implant as claimed in claim 1, wherein the antenna, the stimulation processor and the magnet apparatus are located within a flexible housing.

13. A cochlear implant as claimed in claim 1, wherein the spine and the at least one magnet are formed from different materials.

14. A cochlear implant as claimed in claim 1, wherein the spine is formed from titanium; and
    the at least one magnet is formed from a sintered material.

15. A system, comprising
    a cochlear implant as claimed in claim 1; and
    a headpiece including
    an antenna,
    a housing and disk-shaped positioning magnet that is rotatable relative to the antenna.

16. A as claimed in claim 15, further comprising:
    a sound processor associated with the headpiece.

17. A cochlear implant, comprising:
    a cochlear lead including a plurality of electrodes;
    an antenna;
    a stimulation processor operably connected to the antenna and to the cochlear lead; and
    a magnet apparatus, associated with the antenna, including a case and a magnet assembly, having a spine and at least one magnet that is secured to the spine, that is located within the case and is rotatable relative to the case, wherein the magnet assembly defines a diameter and an outer perimeter and the spine defines a length that is equal to the magnet assembly diameter and includes a web and a pair of flanges with respective curved outer surfaces that form portions of the outer perimeter.

18. A cochlear implant, comprising:
    a cochlear lead including a plurality of electrodes;
    a flexible housing formed from a first material;
    an antenna located within the flexible housing;
    a stimulation processor located within the flexible housing and operably connected to the antenna and to the cochlear lead; and
    a magnet apparatus located within the flexible housing and associated with the antenna, the magnet apparatus including a sealed case, formed from a second material that is different than the first material, and a magnet assembly located within the sealed case, rotatable relative to the sealed case and including a spine and at least one magnet that is secured to the spine and is not rotatable relative to the spine.

19. A cochlear implant as claimed in claim 18, wherein the magnet assembly is rotatable about an axis that defines an axial direction;
    the sealed case includes an internal volume defining a height in the axial direction;

the at least one magnet defines a magnet diameter and a magnet thickness in the axial direction that is less than the internal volume height; and the spine extends continuously in the axial direction and defines a spine thickness in the axial direction that is greater than the magnet thickness.

\* \* \* \* \*